United States Patent [19]

Augustine et al.

[11] Patent Number: 5,106,373
[45] Date of Patent: Apr. 21, 1992

[54] CONVECTIVE WARMING OF INTRAVENOUSLY-ADMINISTERED FLUIDS

[75] Inventors: Scott D. Augustine, Bloomington; Randall C. Arnold, Maplewood, both of Minn.

[73] Assignee: Augustine Medical, Inc., Eden Prairie, Minn.

[21] Appl. No.: 742,057

[22] Filed: Aug. 6, 1991

Related U.S. Application Data

[63] Continuation of Ser. No. 416,399, Oct. 3, 1989, abandoned.

[51] Int. Cl.⁵ .................................................. A61F 7/12
[52] U.S. Cl. ........................................ 604/113; 128/400; 128/402
[58] Field of Search ............... 604/113, 114, 403, 408; 128/399, 400, 402, DIG. 24

[56] References Cited

U.S. PATENT DOCUMENTS

| | | | |
|---|---|---|---|
| 4,531,941 | 7/1985 | Zasuwa | 128/400 X |
| 4,707,587 | 11/1987 | Greenblatt | 604/113 X |
| 4,715,727 | 12/1987 | Carr | 604/113 X |
| 4,874,033 | 10/1989 | Chatelain et al. | 604/113 X |

Primary Examiner—John D. Yasko
Attorney, Agent, or Firm—Baker, Maxham, Jester & Meador

[57] ABSTRACT

IV fluid is warmed while being intravenously-administered to a patient through an IV tube by positioning a portion of the tube at a warming location and flowing a heated gas past the warming location to heat the tube, which thereby heats the IV fluids flowing in the tube.

32 Claims, 3 Drawing Sheets

CONVECTIVE WARMING OF INTRAVENOUSLY-ADMINISTERED FLUIDS

This is a continuation of application Ser. No. 416,399, filed Oct. 3, 1989, now abandoned.

BACKGROUND OF THE INVENTION

The invention is in the field of intravenous administration of fluids to a patient in a clinical setting, and particularly concerns the warming of such fluids while they are being intravenously-administered to a patient.

Fluids which are administered intravenously to a patient consist typically of blood-based fluids and non-blood fluids, all referred to as "IV fluids." As is known, blood-based fluids are held in cool storage at approximately 4° C. until they are used. Non-blood fluids are usually stored at room-temperature.

Intraveneously-administered fluids are a major cause of conductive heat loss in patients and can contribute to patient hypothermia. As is known, hypothermia poses a significant peril in an emergency, and during or after surgery. When fluid must be intraveneously-administered to patients in such circumstances, the threat of hypothermia is compounded.

In the art, it is known to warm fluids prior to administering them intravenously. Further, mechanisms are available for heating fluids during intravenous administration. In one such mechanism, the IV tube used to deliver the fluid is immersed in a liquid, such as a water bath, whose temperature is elevated by an electrical hot plate heater. In another apparatus, a plastic cassette in series with the IV tube is placed against a hot plate to warm the fluid as it runs through the cassette.

All of these methods of fluid warming have limitations. The water bath apparatus is bulky, poses the danger of electrical shock and is inconvenient to use because care must be given to storage and transport of the heating liquid in which the tubing is immersed. The drawbacks of the cassette heater are manifold. The cassette is expensive and it adds resistance to the flow of fluid. The heating element must directly contact the cassette. Because of the high thermal resistance from the element to the cassette, the rate of heating may be insufficient to adequately heat IV fluid flowing at the usual clinical rates. Adjustment of the rate of heating or flow poses the danger of over-heating the fluid, which can damage the components of blood-based compositions.

Therefore, there is an evident requirement for a means and method by which intravenously-administered fluid can be warmed quickly, efficiently, safely, and without the bulkiness and inconvenience of the prior art of warming devices. Preferably, addition of a fluid heating capacity to the normal set of surgical or emergency equipment would not result in a need for extra equipment to heat the fluid.

SUMMARY OF THE INVENTION

The inventor has observed that hypothermia can be effectively combatted by use of convective warming technology as exemplified in U.S. Pat. No. 4,572,188, of which the applicant is a co-inventor. In convective body temperature control technology, a heated gas, such as air, is provided from a source to a thermal blanket or air flow cover which the heated gas inflates and erects. Apertures in the blanket deliver the inflating gas to the patient in the form of a warm bath which uniformly and efficiently elevates the patient's body temperature. This invention is based upon the applicant's critical observation that the flow of heated gas can quickly and efficiently elevate the temperature of an intravenously-introduced fluid while the fluid is being administered to a patient.

A significant objective of this invention is therefore to provide an apparatus and method to heat intravenously-administered fluids by an apparatus which transfers thermal energy from a flowing, heated gas to the fluid during intravenous application.

Advantageously, an apparatus which warms intraveneously-administered fluids by a flow of heated gas eliminates the need for containment of a liquid heating agent and a means to heat the liquid. A gas flow is simple and inexpensive to direct and deliver.

A further advantage is the provision of heated IV fluid without an increase in the usual set of surgical or emergency equipment.

The invention adequately and efficiently heats IV fluid at the IV flow rates encountered in clinical practice without danger to the fluid components.

Other objects and advantages of this invention will become clear when its detailed description is read with reference to the below-described drawings.

DETAILED DESCRIPTION OF THE PREFERRED EMBODIMENTS

Figure 1:
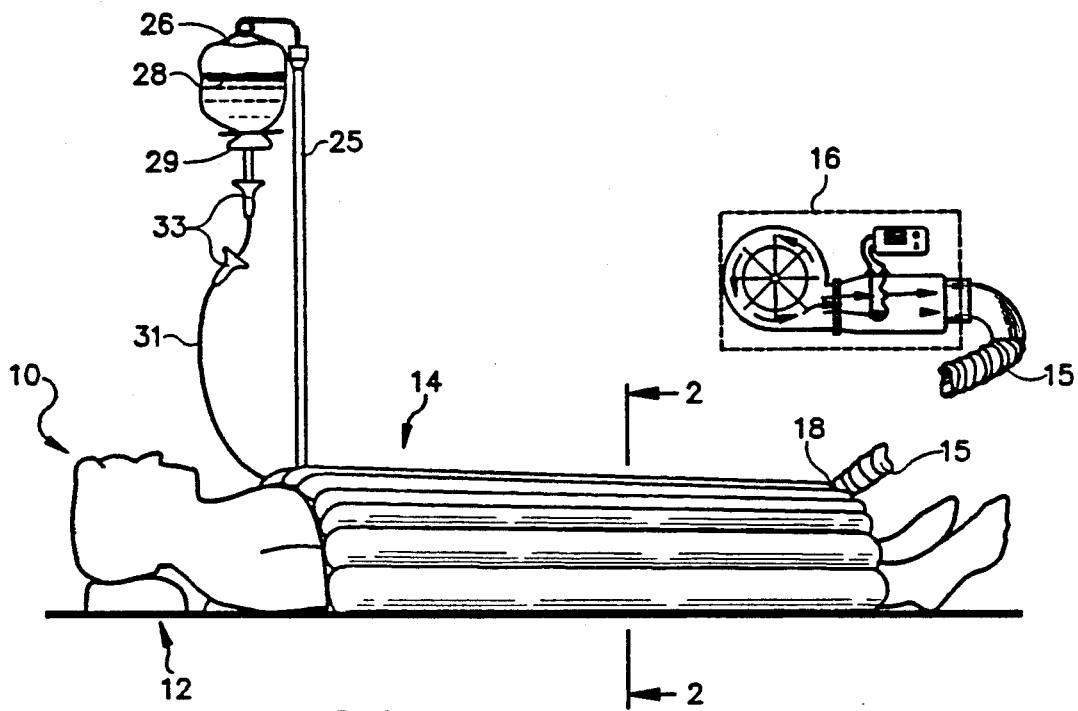
FIG. 1 illustrates an inflatable self-erecting prior art thermal blanket which operates to convectively warm a patient.
Figure 2:
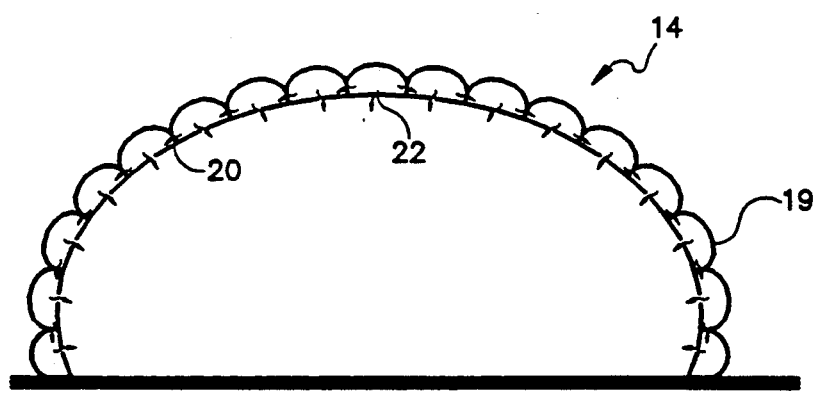
FIG. 2 is a cross section taken along lines 2—2 of FIG. 1.

FIGS. 1 and 2 illustrate an inflatable, self-erecting thermal blanket that is described in detail and claimed in U.S. Pat. No. 4,572,188, which is incorporated herein by reference in its entirety. The thermal blanket of FIGS. 1 and 2 utilizes convection of heated air for temperature management of a patient in a clinical setting. The patient 10 lies on a surface 12. The patient's body temperature is controlled by an inflatable thermal blanket 13, connected by a flexible conduit (hose) 15 to a source of heated air 16. The heated air source 16 heats air and forces a flow of heated air through the conduit 15. The conduit 15 is connected at 18 to the inflatable blanket 14.

As FIGS. 1 and 2 illustrate, the blanket is constructed of a plurality of parallel inflatable chambers, one of which is indicated by reference numeral 19. Each of the chambers 19 has one or more openings to at least one adjacent neighboring chamber so that the heated air forced into the blanket 14 through the conduit 15 flows into all of the chambers. The chambers are made of a flexible material and are inflated when the heated air flows into them. Preferably, the chambers are carried on a relatively flat, non-inflatable undersheet 20. A plurality of apertures are provided which extend through the undersheet 20 into the tubes. One of these apertures is indicated by reference numeral 22.

When the heated air is forced into the blanket, it inflates the chambers, erecting the blanket into the rounded structure illustrated in FIGS. 1 and 2. The inflating heated air flows throughout the chambers and is expelled into the interior of the erected structure through the apertures 22. The expelled air, still heated, bathes and warms the patient 10.

The thermal blanket of FIGS. 1 and 2 is used most frequently in intra-operative, post-operative, or emergency applications. In these situations, patient maintenance frequently requires, in addition to warming, the intravenous administration of fluids, such as blood, blood products, or other IV fluids.

An apparatus for the intravenous adminstration of fluid includes a fluid source consisting of a stand 25 which holds an elevated container 26 of fluid 28. Normally, the container 26 would be an elevated plastic bag if the fluid 28 were blood. If the fluid 28 were a non-blood composition, the container would be either a plastic bag or a bottle. The container 26 is elevated over the patient and held upside down on the stand 25 and its stopper 29 is connected to a valved fluid path including a plastic IV tube 31. The intravenuous connection (not shown) of the tube 31 to the patient is conventional. In operation, the fluid 28 flows out of the container 26 through the tube 31 at a rate which is set by valving 33 in the fluid path.

In order to obviate the cooling effects that cold or room temperature fluid will have on the patient 10, it is useful to warm the fluid 28 as it is being administered. Of course, for the surgical or emergency context illustrated in FIG. 1, it is probable that a host of instrumentation will be connected to the patient 10. Therefore, the addition of the prior art plumbing and heating elements to warm the fluid 28 only adds to the clutter and confusion of instrumentation used with the patient 10.

Figure 3:
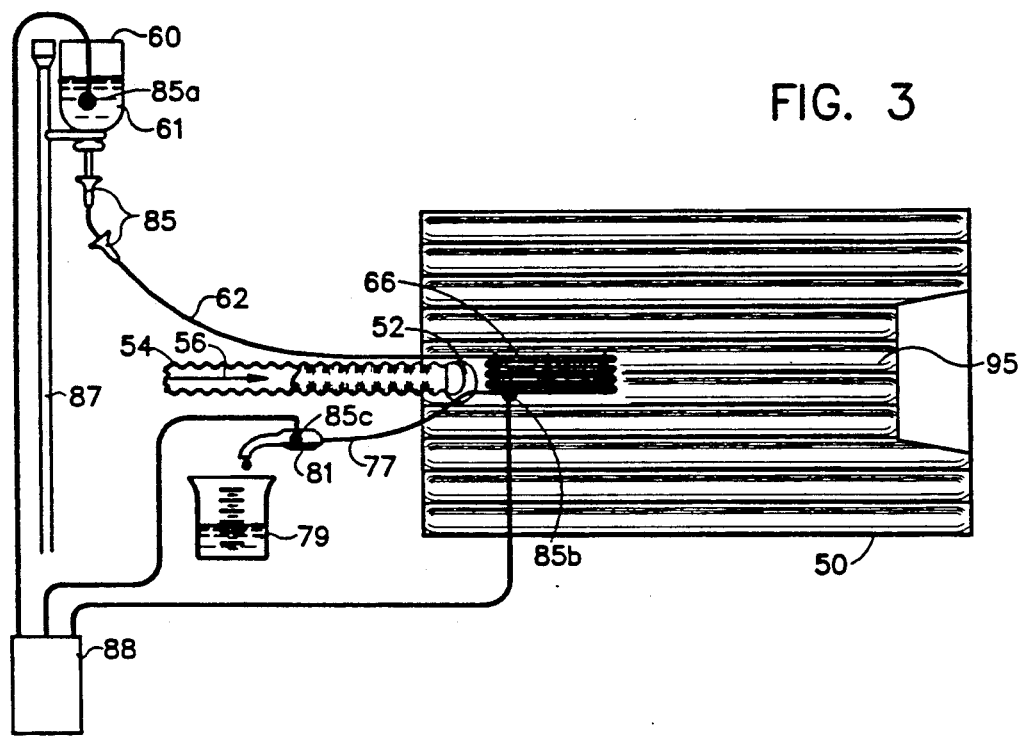
FIG. 3 illustrates a first embodiment of the invention for using heating gas flow to warm intraveneously-administered fluids.
Figure 4A:
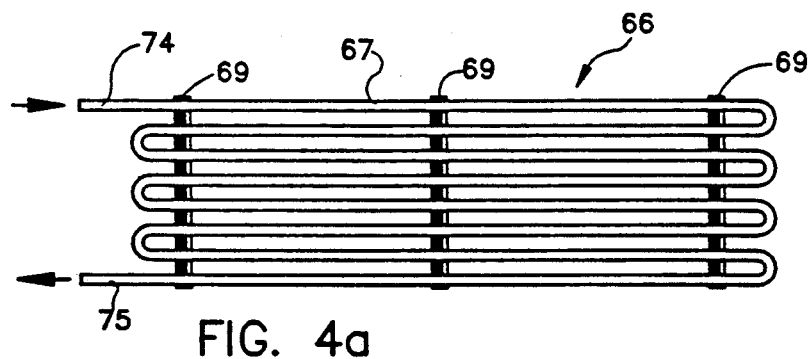
FIGS. 4A and 4B illustrate on an enlarged scale, an apparatus for positioning a portion of an IV tube for warming intravenously-administered fluid.
Figure 4B:
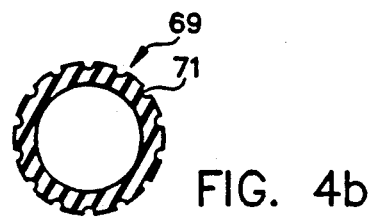

FIGS. 3, 4A, and 4B illustrate a first embodiment for utilizing the flow of heated air generated by the heater/blower 16 to warm intravenously-administered fluid. In FIG. 3, an inflatable self-erecting thermal blanket 50 of the kind illustrated in FIGS. 1 and 2 is connected at 52 to a conduit 54 which delivers heated air flowing in the direction 56 from a heater/blower assembly (not shown). The heated air inflates the blanket 50 in the manner described above, and the inflating air flows out of the under side of the blanket to warm a patient (not shown). An IV fluid 61 is delivered from a container 60 through a tube 62 for conventional intravenous administration to a patient. The fluid flowing in the tube 62 is warmed by an apparatus 66 which is positioned in the center chamber 65 of the thermal blanket 50. The apparatus 66 positions the tube adjacent to the conduit connection 52 at a location in which the inflating heated air flows across and past the tube portion 67. The apparatus 66 is wholly within the center chamber 65 and is warmed by the flow of heated gas which inflates the blanket 50. Warming the tube warms the fluid upstream of the patient; therefore, the fluid is warm when administered to the patient.

FIGS. 4A and 4B illustrate the apparatus 66 which positions the tube portion 67 for warming by the flow of heated air entering the blanket 50 in the conduit 54. As shown in these figures the tube portion 67 is held in a serpentine array by a series of roughly coaxial rings 69. Each of the rings 69 has an outer edge with a set of notches or indentations 71. The rings are aligned, and the tube is snapped into the indentations where it is held to form the serpentine array of tube portion 67. Of course, the serpentine array maximizes the total tube surface area which is exposed to the flow of heated air, which maximizes the amount of heat conducted through the tube to the circulating IV fluid.

FIG. 3 shows a test apparatus by which the inventor has measured the heating effectiveness of the illustrated arrangement. According to FIG. 3, a liquid was conducted through the tube 62 into the serpentine array 67 at 74, and was returned at 75 through the tube section 77. The fluid was collected in a beaker 79 through an outflow valve 81. The flow rate of the liquid through the tube path 62, 66, 77, 81 was set by valving 85. A thermometer 88 was conventionally connected to thermisters 85a in the container 60, 85b in the center chamber 65 adjacent to the tube portion 66, and 85c in the outflow valve 81. The thermometer was conventional, an example being the HH-51 apparatus available from Omega. The thermocouples 85a, 85b, and 85c were conventional K-type thermocouple sensors.

The heating efficiency of the setup of FIG. 3 was tested using chilled ice water in the container 60, which was placed at the top of an IV stand 87, with the termperature probe 85a lowered into the ice water. The valving 85 consisted of inseries, a drip chamber, a 15 drop/minute venoset back check, and a cair clamp IV set all having a combined length of 48 inches. This valving connected the container 60 with the tube 62 and provided the means by which the flow rate of the water was regulated. The IV tube 62 consisted of 168" of 3/16" o.d. ×⅛" i.d. vinyl tube. The tube section 67 was looped into a serpentine array and held on 2" diameter plastic rings, with the loops placed inside the center chamber 65 of the thermal blanket 50. The ambient temperature inside the center chamber 65 was measured by the probe 85b; the outflow temperature of the water was measured at the outflow valve 81 by the probe 85c with the valve 81 placed 12" from the thermal blanket. The results of the test are illustrated in Table I. These results indicate that the first embodiment exhibits highly effective operation in heating a chilled liquid during intravenous administration of the liquid under typical flow rate conditions encountered in everyday clinical environments.

Figure 5:
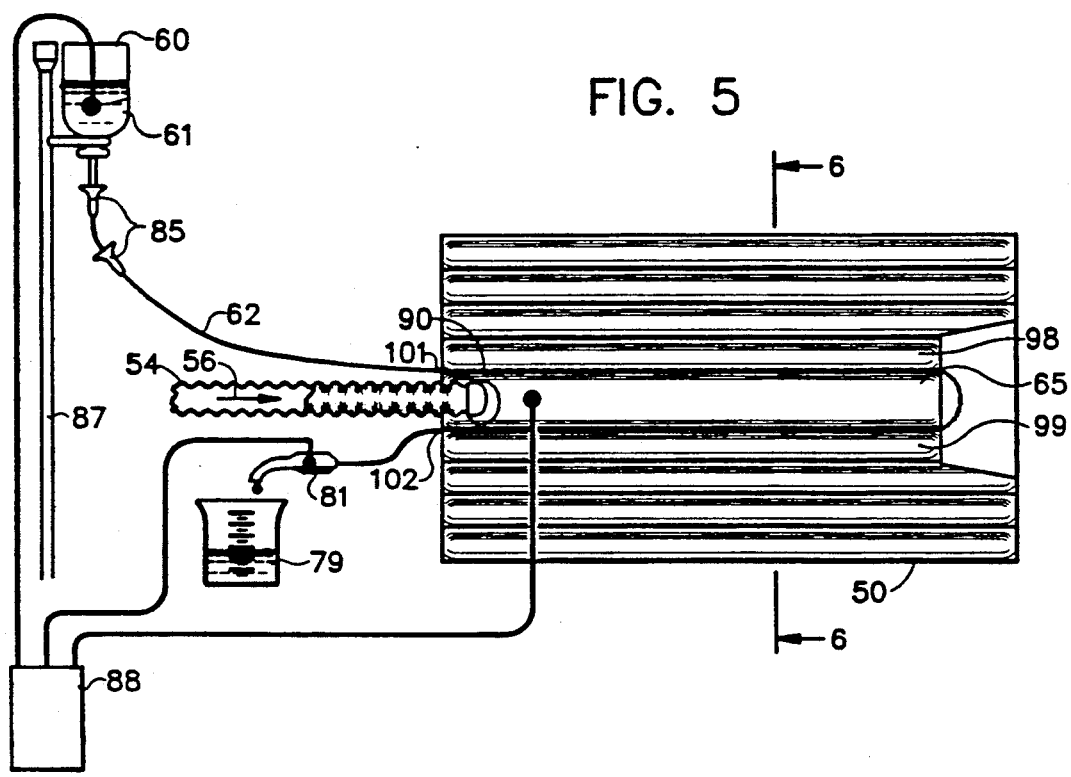
FIG. 5 illustrates a second embodiment of an apparatus which uses a flow of heated gas to warm intravenously-adminstered fluid.
Figure 6:
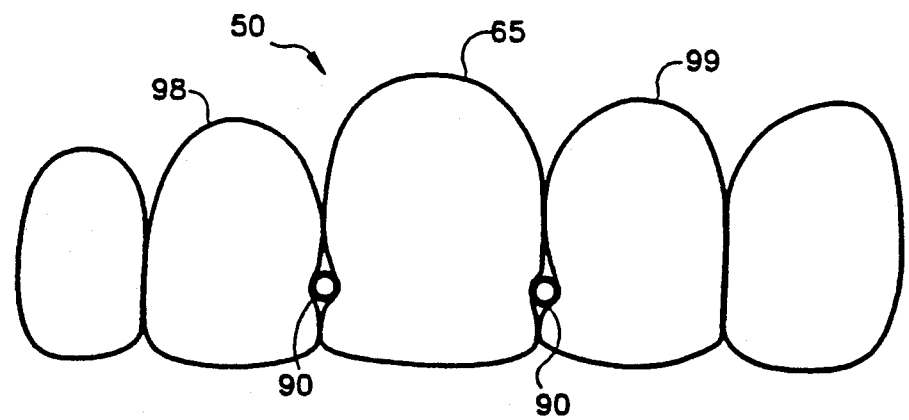
FIG. 6 is an enlarged partial cross-section view taken along the lines 6—6 of FIG. 5 showing how the IV tube is positioned for being warmed.

A second embodiment for using a flow of heated gas to elevate the temperature of an intravenously-administered fluid is illustrated in FIGS. 5 and 6. In FIG. 5, the means for flowing the heated gas (air) is identical with that illustrated in FIG. 3. The means include the thermal blanket 50, the air conduit 54 connected to the center chamber 65 of the blanket 55, and a heater/blower (not shown). In FIG. 5, the tube portion 90 which is heated by the flow of heated air within the blanket 50 is wedged in indentations formed between the center chamber 65 and two other blanket chambers 98 and 99, each abutting one respective side of the center chamber 65. An elongated partial loop of the tube 62 is held in this manner between the tubes 98, 65, and 99 of the blanket. The test setup for measuring the heating efficiency of the second embodiment illustrated in FIG. 5 was the same as that illustrated in FIG. 3. However, the test conditions were varied by using room-temperature water in the container 60. In the test of the FIG. 5 embodiment, the length of the tube portion, measured from point 101 where the tube first contacts the blanket 50 between the chambers 65 and 98 and the point 102 where the tube exits from between the chambers 65 and 99 was varied. Various diameters of the tubing were used for the tube 62. The temperature gain was then measured between the container 60 and the outflow valve 81 for various combinations of lengths and diameters of the tube 62. A cotton hospital blanket (not shown) was placed over the blanket 50 to simulate actual usage of the blanket, but the blanket did not cover the entering or exiting portions of the tube 62. The results of the tests performed for the second embodiment of FIG. 5 are illustrated in Table II. These results indicate that the invention operates very effectively to warm an IV fluid being administered to a patient.

TABLE I

| TEST # | BLANKET TEMP. °F. | INFLOW H₂O TEMP. °F. | OUTFLOW H₂O TEMP. °F. | FLOW RATE liters/hr |
|---|---|---|---|---|
| 1 | 116.8-120.0 | 43.0 | 85.2-85.8 | 2.58 |
| 2 | 116.0-121.2 | 42.6 | 95.2-99.8 | 1.56 |
| 3 | 114.8-121.6 | 43.4 | 104.8-105.2 | .96 |

TABLE II

| TEST # | BLANKET TEMP. °F. | INFLOW H₂O TEMP. °F. | OUTFLOW H₂O TEMP. °F. | FLOW RATE liters/hr | IV TUBE LENGTH inches | IV TUBE OUTER-INNER DIAMETER inches | |
|---|---|---|---|---|---|---|---|
| 1 | 121.4-125.6 | 73.4 | 83.6-84.2 | 1.8 | 80 | 5/32 | 7/64 |
| 2 | 122.6-125.0 | 75.2 | 88.8-90.4 | 1.08 | 80 | 5/32 | 7/64 |
| 3 | 122.2-125.4 | 73.6 | 91.4-91.8 | .9 | 80 | 5/32 | 7/64 |
| 4 | 119.8-121.4 | 75.4 | 85.4-88.2 | 3.1 | 140 | 5/32 | 7/64 |
| 5 | 119.6-121.4 | 76.0 | 96.2-98.4 | 1.0 | 140 | 5/32 | 7/64 |
| 6 | 116.6-118.0 | 76.6 | 81.4-82.0 | 5.6 | 86 | 1/4 | 13/64 |
| 7 | 116.6-118.2 | 76.8 | 87.4-88.2 | 2.1 | 86 | 1/4 | 13/64 |

Those skilled in the art will appreciate the ease and efficiency with which intravenously-administered fluid is heated according to the invention. Use of a flow of heated air results in efficient and very uniform transfer of heat through the IV tubing to the fluid. This conclusion is supported for both of the illustrated embodiments by the results presented in Tables I and II. In both cases, the fluid flow rates were those normally encountered; in both cases, the temperature of fluid flowing in a typical IV set-up was increased significantly; in neither case was the fluid heated above a level which would damage blood components.

Moreover, in a setting where a flowing, heated gas is used to warm a patient, little, or no, additional equipment is required to heat IV fluid with the flowing gas. Although these embodiments show the gas being transported past the IV apparatus by means of a thermal blanket, it should be manifest that other means may be employed to divert and deliver a portion of the gas stream from the heater/blower to the IV tube.

While I have described several preferred embodiments of my invention for convectively warming intravenously-administered fluids, it should be understood that modifications and adapations thereof will occur to persons skilled in the art. Therefore, the protection afforded my invention should only be limited in accordance with the scope of the following claims.

I claim:

1. An apparatus for warming IV fluid during delivery to a patient, which consists of:
   a source of IV fluid;
   a delivery tube connected to said source;
   a means for positioning a respective portion of the delivery tube for warming;
   a source of heated gas; and
   a convective means connected to the source of heated gas for warming the respective delivery tube portion by a flow of heated gas.

2. The apparatus of claim 1 wherein the means for positioning includes a structure for supporting a serpentine array of the respective portion of the delivery tube.

3. The apparatus of claim 2, wherein said structure includes a plurality of annular rings, each ring including a plurality of circumferential indentations, for receiving the delivery tube, each circumferential indentation being an elongate indentation substantially parallel to the axis of its respective annular ring.

4. The apparatus of claim 1 wherein the convective means includes an inflatable thermal blanket.

5. The apparatus of claim 2 wherein the convective means includes an inflatable, convective thermal blanket, said structure being disposed within said blanket.

6. The apparatus of claim 4, wherein the means for positioning includes a plurality of indentations formed in the thermal blanket in response to inflation of the thermal blanket by the heated gas.

7. The apparatus of claim 6, wherein the respective portion of the delivery tube is inserted into the plurality of indentations.

8. An apparatus for heating IV fluid during intravenous administration to a patient, consisting of:
   a tube for intravenously-administering IV fluid;
   a positioner for positioning the tube for heating; and
   a means for flowing a heated gas past the positioner to heat the tube.

9. The apparatus of claim 8, wherein the positioner includes a structure for supporting a serpentine array of a respective portion of the tube.

10. The apparatus of claim 9, wherein the positioner includes a plurality of annular rings, each ring including a plurality of circumferential indentations for receiving the tube, each circumferential indentation being an elongated indentation substantially parallel to the axis of its respective annular ring.

11. The apparatus of claim 8, wherein the means for flowing includes an inflatable thermal blanket.

12. The apparatus of claim 9, wherein the means for flowing includes an inflatable, convective thermal blanket, said positioner being disposed within said blanket.

13. The apparatus of claim 11, wherein the positioner includes a plurality of indentations formed in the thermal blanket in response to inflation of the thermal blanket by said heated gas.

14. The apparatus of claim 13, wherein a respective portion of the tube is inserted into the plurality of indentations.

15. A method for warming IV fluid during delivery to a patient using an apparatus including a source of IV fluid and a delivery tube connected to said source for intravenously-administering the IV fluid to the patient, the method comprising the steps of:

positioning a respective portion consisting of the delivery tube at a warming location; and flowing a heated gas past said warming location to heat said delivery tube.

16. The method of claim 15 wherein said apparatus includes an inflatable thermal blanket and a source of heated air connected to said thermal blanket for delivering heated air to inflate said thermal blanket, said thermal blanket connectively heating said patient with said heated air upon being inflated, said positioning step including the step of placing said respective portion of the delivery tube in said thermal blanket.

17. The method of claim 16, wherein said placing step includes inserting said respective portion of the delivery tube in a fold of the thermal blanket.

18. The method of claim 16, wherein said placing step includes positioning said respective portion of the delivery tube inside of the thermal blanket.

19. An apparatus for warming IV fluid during delivery to a patient, which comprises:

a source of IV fluid;

a delivery tube connected to said source;

a convective means connected to the source of heated gas for providing a flow of heated gas; and a heat transfer mechanism consisting of a respective portion of the delivery tube and means cooperating with the convective means for positioning the respective portion of the delivery tube at the flow of heated gas.

20. The apparatus of claim 19, wherein the means for positioning includes a structure for supporting a serpentine array of the respective portion of the delivery tube.

21. The apparatus of claim 20, wherein said structure includes a plurality of annular rings, each ring including a plurality of circumferential indentations for receiving the delivery tube, each circumferential indentation being an elongated indentation substantially parallel to the axis of its respective annular ring.

22. The apparatus of claim 19, wherein the convective means includes an inflatable thermal blanket.

23. The aparatus of claim 20, wherein the convective means includes an inflatable, convective thermal blanket, said structure being disposed within said thermal blanket.

24. The apparatus of claim 22, wherein the means for positioning includes a plurality of indentations formed in the thermal blanket in response to inflation of the thermal blanket by the heated gas.

25. The apparatus of claim 24, wherein the respective portion of the delivery tube is inserted into the plurality of indentations.

26. An apparatus for heating IV fluid during intravenous administration to a patient, comprising:

an IV tube apparatus including an IV fluid source and an IV tube for intravenously-administered IV fluid;

a heat transfer mechanism consisting only of a portion of the IV tube;

a positioner for positioning the heat transfer mechanism for convective heating; and a means for flowing a heated gas past the positioner to heat the IV tube portion.

27. The apparatus of claim 26, wherein the positioner includes a structure for supporting a serpentine array of the respective portion of the IV tube.

28. The apparatus of claim 27, wherein the positioner includes a plurality of annular rings, each ring including a plurality of circumferential indentations for receiving the IV tube, each circumferential indentation being an elongated indentation substantially parallel to the axis of its respective annular ring.

29. The apparatus of claim 26, wherein the means for flowing includes an inflatable thermal blanket.

30. The apparatus of claim 27, wherein the means for flowing includes an inflatable, convective thermal blanket, said positioner being disposed within said blanket.

31. The apparatus of claim 29, wherein the positioner includes a plurality of indentations formed in the thermal blanket in response to inflation of the thermal blanket by said heated gas.

32. The apparatus of claim 31, wherein the portion of the tube is inserted into the plurality of indentations.

* * * * *